United States Patent
Suri

(10) Patent No.: US 10,149,965 B2
(45) Date of Patent: Dec. 11, 2018

(54) SHAPE MEMORY GUIDE WIRE

(71) Applicant: Cook Medical Technologies LLC, Bloomington, IN (US)

(72) Inventor: Himanshu Suri, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 391 days.

(21) Appl. No.: 14/325,864

(22) Filed: Jul. 8, 2014

(65) Prior Publication Data

US 2015/0018716 A1    Jan. 15, 2015

Related U.S. Application Data

(60) Provisional application No. 61/844,943, filed on Jul. 11, 2013.

(51) Int. Cl.
    *A61M 25/09*    (2006.01)

(52) U.S. Cl.
    CPC ... *A61M 25/09* (2013.01); *A61M 2025/09083* (2013.01); *A61M 2025/09141* (2013.01)

(58) Field of Classification Search
    CPC ........ A61M 25/09; A61M 2025/09175; A61M 2025/09083
    See application file for complete search history.

(56) References Cited

U.S. PATENT DOCUMENTS

| | | | |
|---|---|---|---|
| 4,940,062 A | 7/1990 | Hampton et al. | |
| 4,984,581 A | 1/1991 | Stice | |
| 4,991,602 A | 2/1991 | Amplatz et al. | |
| 5,090,956 A | 2/1992 | McCoy | |
| 5,147,370 A * | 9/1992 | McNamara | A61F 2/88 606/108 |
| 5,203,772 A | 4/1993 | Hammerslag et al. | |
| 5,209,735 A | 5/1993 | Lazarus | |
| 5,231,989 A | 8/1993 | Middleman et al. | |
| 5,238,004 A | 8/1993 | Sahatjian et al. | |
| 5,341,818 A | 8/1994 | Abrams et al. | |
| 5,433,200 A * | 7/1995 | Fleischhacker, Jr. | A61M 25/09 600/434 |
| 5,624,508 A * | 4/1997 | Flomenblit | C22F 1/006 148/510 |
| 5,944,701 A | 8/1999 | Dubrul | |
| 6,348,067 B1 * | 2/2002 | Baum | A61M 25/0068 606/191 |
| 2002/0185200 A1 * | 12/2002 | DiCarlo | C22F 1/006 148/563 |

(Continued)

*Primary Examiner* — Sean Dougherty
*Assistant Examiner* — Patrick Fernandes
(74) *Attorney, Agent, or Firm* — Brinks Gilson & Lione

(57) ABSTRACT

A guide wire is described for navigating body channels such as vessels. The guide wire can include an elongated member having a proximal portion and a distal portion, and a fluid passage to transport a fluid from the proximal portion to the distal portion. The distal portion of the elongated member can include a shape memory material with two way memory effect. The shape memory material can have a transition temperature less than a body temperature such that the distal portion has a first shape at the body temperature and a second shape different from the first shape at a temperature less than the transition temperature.

20 Claims, 4 Drawing Sheets

(56) References Cited

U.S. PATENT DOCUMENTS

2006/0253114 A1\* 11/2006 Saadat ................... A61B 18/02
  606/21
2010/0078123 A1\* 4/2010 Huang ....................... C09J 5/02
  156/244.23

\* cited by examiner

SHAPE MEMORY GUIDE WIRE

This application claims priority to U.S. Provisional Application No. 61/844,943, filed Jul. 11, 2013, which is hereby incorporated by reference herein.

BACKGROUND

The present invention relates generally to medical devices and more particularly to guide wires.

Often elongated, flexible guide wires are used to gain access to specific inner areas of the body. The guide wire may enter the body through a small opening and travel to parts of the body through body channels. For example, guide wires may be passed through the body via peripheral blood vessels, gastrointestinal tract, or the urinary tract, and guide wires are currently used in cardiology, gastroenterology, urology, and radiology. Once the guide wire is at a target site in the body, guide wires are commonly used as guides for the introduction of additional medical instruments such as catheters.

Body channels are often tortuous, so the guide wire may be difficult to navigate through the channels. Guide wires generally have a distal portion that has a fixed shape that is either straight or curved. The fixed shape distal portion can be difficult to traverse body channels. In particular, moving the guide wire into a branch section of a body channel can be difficult with a fixed shape. Accordingly, further improvements and enhancements for guide wires are desirable.

SUMMARY

A guide wire is described for navigating body channels such as vessels. The guide wire can include an elongated member having a proximal portion and a distal portion, and a fluid passage to transport a fluid from the proximal portion to the distal portion. The distal portion of the elongated member can include a shape memory material with two way memory effect. The shape memory material can have a transition temperature less than a body temperature such that the distal portion has a first shape at the body temperature and a second shape different from the first shape at a temperature less than the transition temperature. The inventions herein may also include any other aspect described below in the written description, the claims, or in the attached drawings and any combination thereof.

BRIEF DESCRIPTION OF THE DRAWINGS

The invention may be more fully understood by reading the following description in conjunction with the drawings, in which.

DETAILED DESCRIPTION

Figure 1:
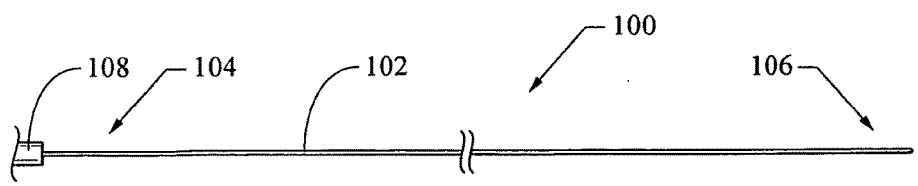
FIG. 1 is a side view of a guide wire.

Referring now to the figures, and particularly to FIG. 1, a guide wire 100 that includes an elongated member 102 having a proximal portion 104 and a distal portion 106 is shown. The elongated member 102 can, for example, have an outer diameter of about 0.2 mm to about 2 mm or about 0.4 mm to about 1.4 mm and have a length of about 20 cm to about 600 cm or about 50 cm to about 300 cm. The elongated member 102 can be coupled to a fluid supply 108 such as a handle. As discussed further below, the fluid supply 108 can provide a fluid to the elongated member 102.

Figure 2A:
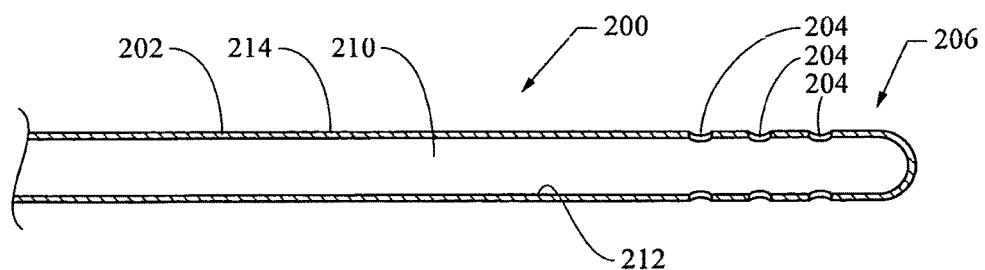
FIG. 2A is a cross-sectional side view of a distal portion of a guide wire comprising a shape memory material having a first shape.
Figure 2B:
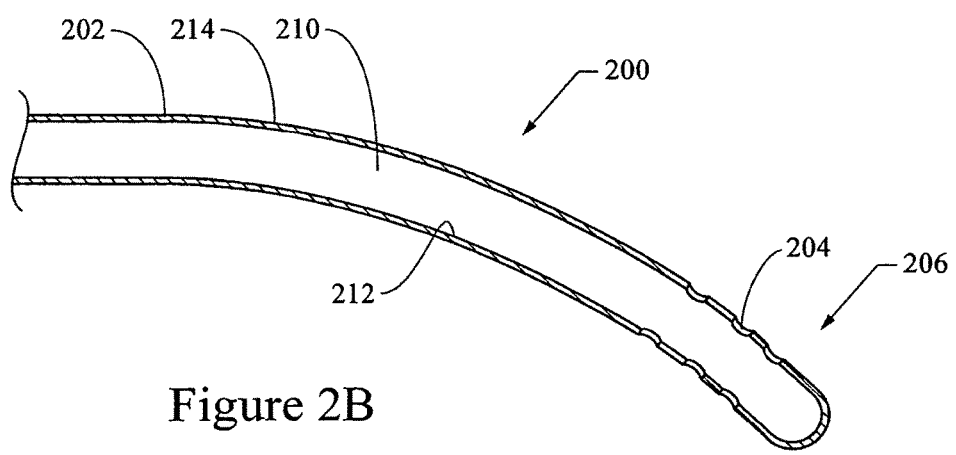
FIG. 2B is a cross-sectional side view of the distal portion of the guide wire of FIG. 2A having a second shape.

FIG. 2A is a cross-sectional view of a distal portion 206 of an elongated member 202 of a guide wire 200. The guide wire 200 can include a fluid passage 210 to transport a fluid from the proximal portion to the distal portion 206. The distal portion 206 of the elongated member 202 can include or be a shape memory material with a two way memory effect. The entire elongated member 202 may also be a shape memory material. The shape memory material can have a transition temperature less than a body temperature such that distal portion 206 has a first shape at the body temperature and a second shape different from the first shape at a temperature less than the transition temperature. For example, FIG. 2B shows the distal portion 206 with a shape different than that of FIG. 2A. Thus, the shape of the distal portion 206 of FIG. 2A can be the first shape and the shape of the distal portion 206 of FIG. 2B can be the second shape. Alternatively, the shape of the distal portion 206 of FIG. 2B can be the first shape and the shape of the distal portion 206 of FIG. 2A can be the second shape. A fluid having a fluid temperature less than the body temperature can be flowed or flushed through the fluid passage 210 to cool the distal portion 206 to below body temperature. For instance, the fluid temperature can be equal to or less than the transition temperature to cool the distal portion 206 to or below the transition temperature. For example, the fluid can have a temperature less than body temperature or 37° C.

By being able to control the shape of the distal portion 206, the guide wire 200 can be more easily navigated through a tortuous or angulated path of a body channel. For example, the distal portion 206 can be generally straight so that the guide wire 200 can move through a relatively straight body channel. If the guide wire 200 is desired to move into a branch from the body channel such as a branch that is generally perpendicular to the body channel, the shape of the distal portion 206 can be selectively changed at the branch. For example, the distal portion 206 can change into a curved shape so that the guide wire 200 can more easily be manipulated to move into the branch.

The shape memory material can be one or more of various types such as alloys and polymers. One exemplary class of shape memory alloys is nickel-titanium (NiTi) alloys, also known as nitinol. Nitinol is a metal alloy composition that includes nickel and titanium. However, nitinol can also include various other alloying elements such as cobalt, chromium and/or erbium. For example, nitinol can have a composition according to ASTM F2063. Upon cooling, nitinol transforms from having an austenite phase to having a martensite phase. The change from austenite to martensite is the reason that nitinol can have a shape-memory effect.

The shape-memory effect can be instilled into nitinol by providing the nitinol having a first shape. The nitinol can be deformed into a second shape while the crystal structure is martensite. Upon reheating the nitinol to have the austenite crystal structure, the nitinol will change from the second shape to the first shape.

The shape-memory effect of the shape memory material can be one-way or two-way. For one-way memory effect, upon heating nitinol from martensite to austenite and the second shape changing to the first shape, the shape memory material will not change shape again upon further phase changes from additional heating or cooling. However, shape memory material can have two-way memory effect such that the shape memory material can go through a plurality of martensite to austenite to martensite phase changes with shape changes still occurring through each martensite to austenite and austenite to martensite phase change. Thus, the shape memory material with two way memory effect can have at least a first shape while martensite and a second shape while austenite and maintain the distinct shapes even after a plurality of phase change cycles between martensite and austenite. Thus, in contrast to one-way memory effect in which the shape memory alloy must, after being heated to the austenite phase, be mechanically deformed while in the martensite phase to re-impart a shape memory effect, two-way can maintain the shape memory effect, after being heated to the austenite phase, without having to be mechanically deform again. In other words, two-way effect shows exhibits shape change upon both cooling and heating while one-way effect only exhibits shape change upon heating.

Under typical circumstances, nitinol will only have a one-way memory effect such that nitinol will return to a high temperature shape but will not return to a low temperature shape. However, the two-way effect can be imparted to nitinol by training the nitinol to also change shape upon cooling. For example, the training of nitinol can include a process of deforming the nitinol while the nitinol has a martensite phase, heating the nitinol to an austenite phase, cooling the nitinol to the martensite phase, and repeating these steps a plurality of times to acquire a two-way memory effect. The training can also be done in one step, but may be dependent on alloy composition. For example, the nitinol can be heated to about 500° C. for about 10 minutes and cooled in an iced water bath. The nitinol may be mechanically deformed at room temperature and return to the nitinol's pre-deformed shape by heating the nitinol to a temperature to form the austenite phase.

Figure 3:
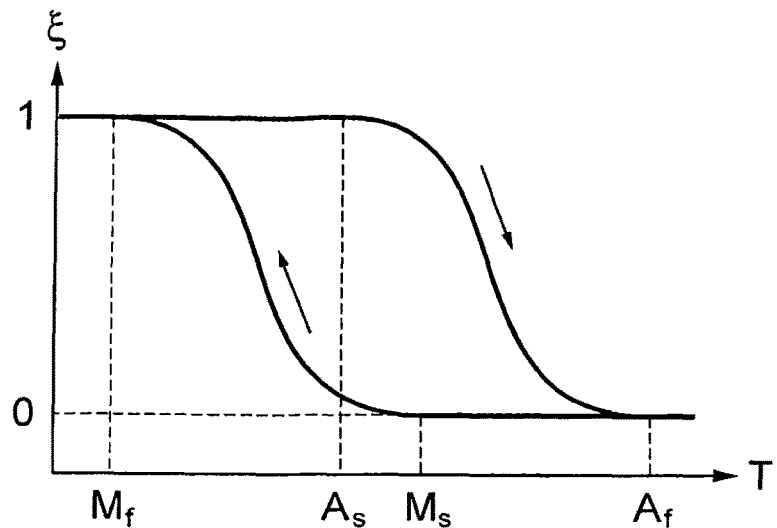
FIG. 3 is a plot of fraction of martensite phase as a function of temperature for a shape memory alloy.

In addition, transition between martensite and austenite does not typically occur at a specific temperature but instead, over a temperature range. FIG. 3 is a plot of fraction of martensite as a function of temperature. Upon heating from martensite to austenite, austenite begins to form at temperature $A_s$ and completes transformation to austenite at temperature $A_f$. Upon cooling from martensite to austenite, martensite beings to form at temperature $M_s$ and completes transformation to martensite at temperature $M_f$. As shown in FIG. 3, the cooling and heating cycle shows thermal hysteresis as a result of mechanical energy lost in the process. Thus, temperature $A_s$ is not necessarily equal to temperature $M_f$, and temperature $A_f$ is not necessarily equal to temperature $M_s$. Thus, the transition temperature may actually be a temperature range such as a range of about 15° C. to about 20° C. However, transition temperature as used herein refers to a temperature in which at least some change in shape due to the shape memory effect occurs upon heating from a first temperature to a second temperature or in which at least some change in shape due to the shape memory effect occurs upon cooling from a first temperature to a second temperature.

For example, the transition temperature for nitinol can be $A_f$. Thus, the body temperature can be above $A_f$. When the transition temperature is $A_f$, complete phase change between martensite and austenite can occur. Thus, complete shape change from a first shape to a second shape can occur. For instance, the distal portion can be inserted into a body channel and the distal portion can have a temperature equal to body temperature. At body temperature, the nitinol can be completely austenite and have a first shape. The nitinol can then be cooled, and the austenite can change to martensite. At $M_s$, the nitinol begins to form martensite, and at $M_f$, the nitinol becomes completely martensite. However, the nitinol may not be cooled to $M_f$ since some shape change would occur at temperatures below $M_s$. Upon reheating back to body temperature, any martensite would change to austenite. Alternatively, the distal portion can be cooled prior to and during being inserted into the body channel so that the nitinol can be at least some martensite. After insertion into the body, cooling to the distal portion can be slowed or stopped so that the temperature of distal portion can rise so that at least some of the martensite changes to austenite.

In another example, the transition temperature for nitinol can be $M_s$. Thus, the body temperature can be above $M_s$, or can be between $M_s$ and $A_f$. When the body temperature is between $M_s$ and $A_f$, complete transformation from martensite to austenite may not occur upon heating from a temperature in which the nitinol has at least some martensite. However, at least some change in shape can occur since at least some phase change can occur. For instance, when the nitinol is at body temperature, at least a portion of the nitinol can be austenite. Upon cooling to below $M_s$, at least some of the austenite can change to martensite; thus, at least some shape change can occur. Furthermore, upon heating from a temperature below $M_s$ to body temperature, at least some martensite of the nitinol can change to austenite.

In a further example, the transition temperature for nitinol can be $A_s$. Thus, the body temperature can be above $A_s$, can be between $A_s$ and $A_f$, or can be between $A_s$ and $M_s$. Similar to when the transition temperature is $M_s$, at least some change in shape can occur since at least some phase change can occur. For instance, when body temperature is between $A_s$ and $A_f$, or between $A_s$ and $M_s$ and when the nitinol is at body temperature, at least a portion of the nitinol can be austenite. Upon cooling to below $A_s$, at least some of the austenite can change to martensite; thus, at least some shape change can occur. Furthermore, upon heating from a temperature below $A_s$ to body temperature, at least some martensite of the nitinol can change to austenite.

In an even further example, the transition temperature for nitinol can be $M_f$. Thus, the body temperature can be above $M_f$, can be between $M_f$ and $A_f$, can be between $M_f$ and $M_s$, or can be between $M_f$ and $A_s$. When the body temperature is between $M_f$ and $A_s$, the nitinol may not change at all to austenite when heating the nitinol from $M_f$. However, if the nitinol has at least some austenite, upon cooling from body temperature, at least some of the austenite can transform to martensite. However, after the austenite changed to martensite, the martensite would not change to austenite upon heating to body temperature since in this example, body temperature is below $A_s$.

Furthermore, the transition temperature can be selected by selecting a particular alloy composition. For example, the $M_f$, $A_s$, $M_s$ and/or $A_f$ can be selected by selecting a nitinol composition that is either nickel rich or titanium rich from stoichiometric NiTi. For instance, $A_f$ can be controlled by the composition of nickel in the nitinol composition, and $A_f$ may be directly proportional to the percentage of nickel in the nitinol composition. In one example, nickel concentration may be between about 50.4 and about 50.8 weight percent.

As described above, the transition temperature can be less than the body temperature. Thus, the transition temperature can be less than 37° C. However, the transition temperature may be further away from the body temperature such as less than about 36° C. or less than about 30° C. However, the closer the transition temperature is to body temperature the quicker the distal portion 206 can be cooled to the transition temperature. Thus, the transition temperature may be greater than about 20° C. or greater than about 30° C.

The distal portion 206 can be a section of the guide wire 200 that has a two-way shape memory effect. Thus, the proximal portion may not be configured to have a two-way shape memory effect. For example, the distal portion 206 can have a length of about 10 mm to about 10 cm. The proximal portion can be the remainder of the elongated member 202.

As discussed above, the fluid passage 210 can transport a fluid from the proximal portion to the distal portion 206 of the guide wire 200. Therefore, the fluid passage 210 can extend from the proximal portion to the distal portion 206. The fluid passage 210 can be within the elongated member 202. As such, the elongated member 202 can have a tubular shape with the fluid passage 210 being defined by inner walls 212 of the elongated member 202. Alternatively, the fluid passage 210 can be separate from the elongated member 202.

In order cool the distal portion 206 of the guide wire 200, the distal portion 206 can have one or more ports 204. For example, the ports 204 can be spaced along the distal portion 206 and/or a port 204 can be disposed on the distal end. The ports 204 can extend from the fluid passage 210 to an outer surface 214 of the elongated member 202. Thus, the fluid passage 210 can be in fluid communication with a volume such as a vessel that the distal portion 206 is within. The fluid can flow through the fluid passage 210 from the proximal portion to the distal portion 206 and out of the distal portion 206. Therefore, the fluid can continuously flow in order to continuously cool the distal portion 206, or the fluid can be selectively stopped and started in order to control the shape of the distal portion 206. The amount of surface area that the ports 204 cover on the outer surface 214 can affect the flow rate of the fluid out of the distal portion 206. Thus, the surface area of the ports 204 can be increased to increase flow rate of the fluid and therefore the cooling rate of the fluid. For example, the ports 204 or openings can cover between 10% and 75% of the outer surface area of the distal portion 206. The ports 204 can have a diameter of about 0.25 mm to about 1.0 mm. The distal portion 206 can have about 1 to about 10 or more ports 204.

Various fluids can be flowed through the fluid passage 210. For example, fluids that are nontoxic such as saline solution or radio contrast solution can be used. Radio contrast solution, in addition to cooling the distal portion 206, can be used to also image vessels (e.g., fluoroscopy) and/or locate the distal portion 206 within a patient. For example, the distal portion 206 can include a radiopaque marker. Therefore, since the guide wire 200 with the shape-changing distal portion 206 can navigate angulated body channels more quickly, the time to reach a target site can be reduced. Thus, the amount of fluoroscopy a patient is exposed to can be reduced. As previously discussed, the temperature of the fluid that is flowed through the fluid passage 210 can be selected based on the transition temperature and shape memory properties of the shape memory material.

Figure 4A:
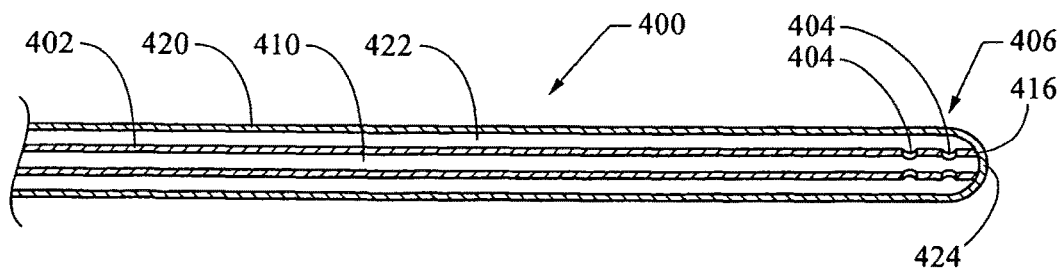
FIG. 4A is a cross-sectional side view of a distal portion of a guide wire configured to recirculate a cooling fluid having a first shape.
Figure 4B:
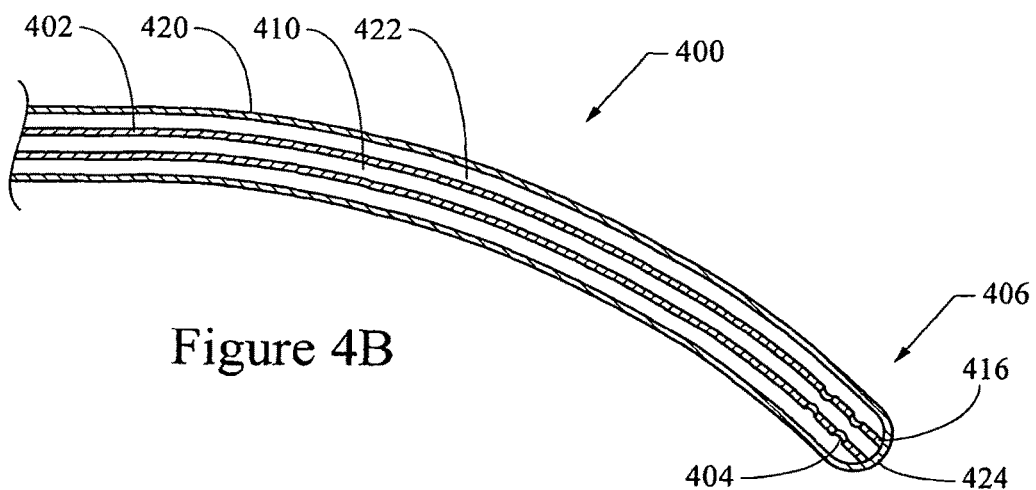
FIG. 4B is a cross-sectional side view of the distal portion of the guide wire of FIG. 2B having a second shape.

Alternatively to flowing the fluid into a vessel, the fluid can be transported back to the proximal portion of a guide wire by a return passage. For instance, the fluid passage can be fluidly isolated or fluidly sealed from the body channel. FIGS. 4A and 4B illustrate an example guide wire 400 configured to return fluid to the proximal portion. FIGS. 4A and 4B show the distal portion 406 of the guide wire 400 having two possible different shapes that can be obtained as a result of shape memory material. The guide wire 400 can include an outer member 420 having a secondary passage 422. The elongated member 402 can be at least partially disposed within the secondary passage 422. The distal end 416 of the elongated member 402 may extend to and be engaged or attached to the distal end 424 of the outer member 420, as shown in FIGS. 4A and 4B, or the distal end 416 of the elongated member 402 may be spaced from the distal end 424 of the outer member 420. The elongated member 402 and the outer member 420 can also have other configurations so that fluid can flow from the proximal end to the distal end and then return to the proximal end.

The distal portion 406 of the elongated member 402 can include one or more ports 404 so that the fluid passage 410 is in fluid communication with the secondary passage 422. Fluid can be flowed through the fluid passage 410 from the proximal portion to the distal portion 406, and then the fluid can be flowed through the secondary passage 422 from the distal portion 406 to the proximal portion. Alternatively, fluid can be flowed through the secondary passage 422 from the proximal portion to the distal portion 406, and then the fluid can be flowed through the fluid passage 410 from the distal portion 406 to the proximal portion. In another example, when the distal end 416 of the elongated member 402 is spaced from the distal end 424 of the outer member 420, the port 404 can be on the distal end 416 of the elongated member 402.

The distal portion 406 of the elongated member 402 and/or the outer member 420 can be or include a shape memory material such as those described above. Thus, both or only one of the elongated member 402 and the outer member 420 may include a shape memory material. For example, only one of the elongated member 402 or the outer member 420 includes a shape memory material while the other of the elongated member 402 or the outer member 420 does not include a shape memory material. Thus, the one of the elongated member 402 or the outer member 420 that does not include a shape memory material can include a non-shape memory material. The non-shape memory material can be deformable so that when the shape memory material changes shape, the non-shape memory material can deform so that the distal portion 406 of the guide wire 400 can change shape as a result of the shape memory material.

Figure 5A:
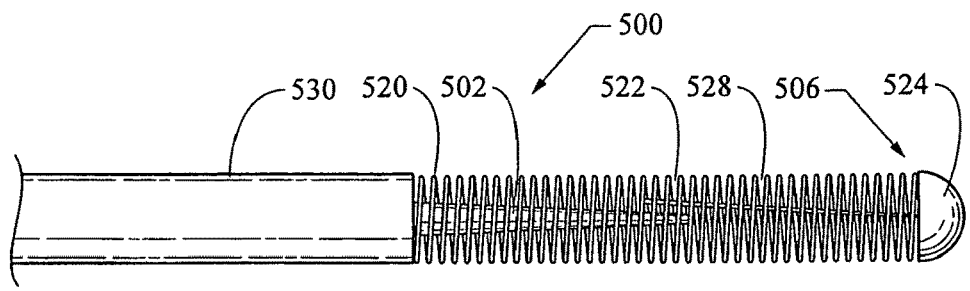
FIG. 5A is a side view of a distal portion of a guide wire that includes an elongated member disposed within an outer member having a first shape.
Figure 5B:
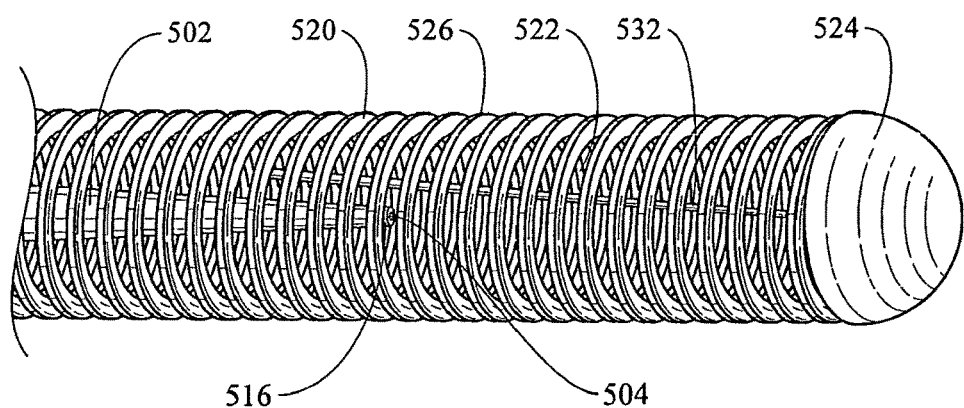
FIG. 5B is a perspective side view of the distal portion of the guide wire of FIG. 5A showing a port in the distal end of the elongated member.
Figure 5C:
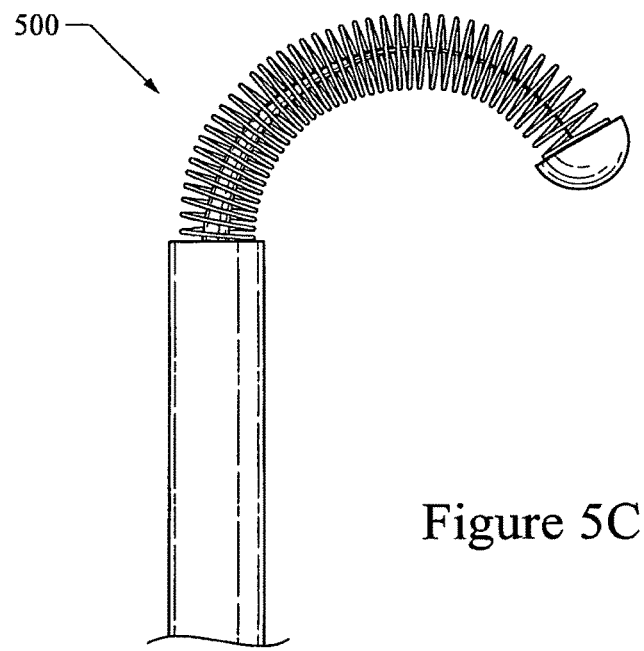
FIG. 5C is a side view of the distal portion of the guide wire of FIG. 5A having a second shape.
Figure 6A:
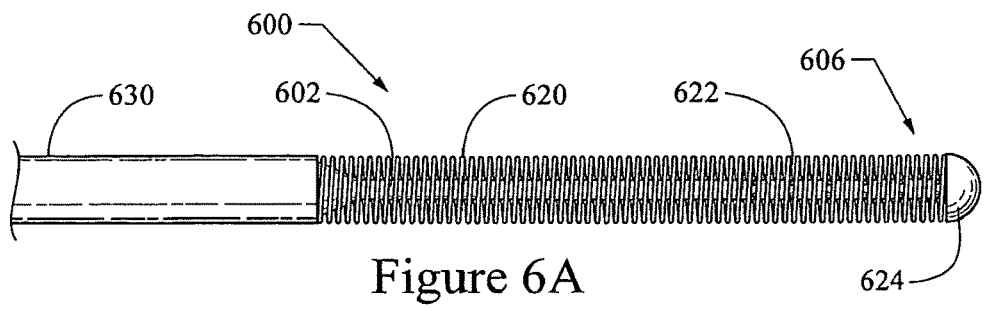
FIG. 6A is a side view of a distal portion of a guide wire that includes an elongated member disposed within an outer member and the elongated member extending to the distal end of the outer member having a first shape.
Figure 6B:
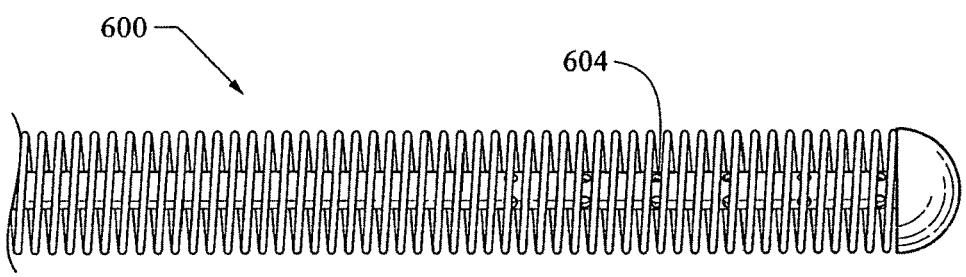
FIG. 6B is a magnified side view of the distal portion of the guide wire of FIG. 6A showing a plurality of ports on the distal portion of the elongated member.
Figure 6C:
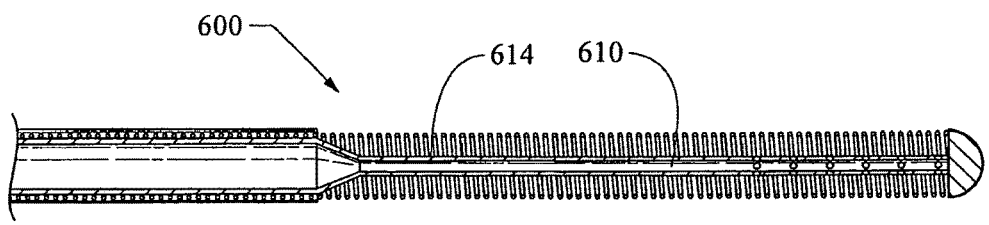
FIG. 6C is a cross-sectional side view of the guide wire of FIG. 6A.
Figure 6D:
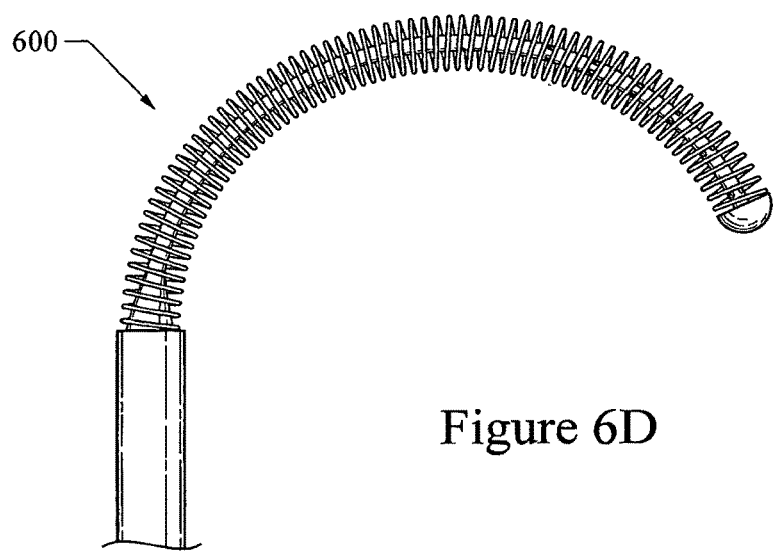
FIG. 6D is a side view of the distal portion of the guide wire of FIG. 6A having a second shape.

A guide wire 500 can include an outer member 520 that is configured to permit fluid to flow therethrough, as illustrated in FIGS. 5A-5C, instead of containing fluid as described with regard to FIGS. 4A and 4B. The outer member 520 can have a secondary passage 522, and the elongated member 502 can be at least partially disposed within the secondary passage 522. The outer member 520 can include an opening 528 extending from the secondary passage 522 to an outer surface 526 of the outer member 520. For example, as illustrated in FIGS. 5A-5C, the outer member 520 can be a coil having windings spaced a distance from one another. The opening 528 can include the spaces between the windings. The outer member 520 can extend from the distal end 524 to the proximal end of the guide wire 500. The proximal portion of the guide wire 500 may include a sheath 530 that covers the outer member 520. Therefore, the distal portion 506 of the outer member 520 can be uncovered by the sheath 530, and the opening 528 may only be on the distal portion 506 and not the proximal portion of the guide wire 500. The sheath 530 can comprise or be a polymer such as polytetrafluoroethylene or nylon.

The distal portion 506 of the elongated member 502 can be radially spaced inward from the outer member 520 a distance. As illustrated in FIGS. 5A-5C, the distal end 516 of the elongated member 502 can be laterally spaced from the distal end 524 of the outer member 520 such that distal end 516 of the elongated member 502 is within the secondary passage 522. Alternatively, as further discussed below with regard to FIGS. 6A-D, the elongated member 502 can extend to the distal end 524 of the outer member 520. A port 504 is illustrated in FIGS. 5A-5C as being at the distal end 516 of the elongated member 502. However, one or more ports 504 can be disposed at other locations on the distal portion 506 of the elongated member 502.

The outer member 520 can include a support member 532 such as a support wire to provide additional structural support to the distal portion 506 of the outer member 520. For example, when the outer member 520 is a coil, the coil may bend and change shape with relatively small amounts of force. Therefore, the support member 532 can be coupled between a plurality of windings to increase the rigidity of the coil.

To cool the distal portion 506, fluid can be flowed through the fluid passage of the elongated member 502, out of the port 504, into the secondary passage 522, through the opening 528, and out of the distal portion 506 of the guide wire 500. FIG. 5C illustrates an exemplary shape change as a result of cooling compared to the shape shown in FIG. 5A. In particular, the outer member 520 can comprise a shape memory material since the outer member 520 extends longitudinally beyond the elongated member 502 so the distal portion 506 beyond the elongated member 502 can curve or change shape. Alternatively, the guide wire 500 may not include an elongated member 502, and instead, the outer member 520 is effectively the elongated member 502. To cool the distal portion 506, fluid may be flowed through the secondary passage 522 which would effectively be the fluid passage and out the opening 528 of the outer member 520.

FIGS. 6A-6D illustrate another exemplary guide wire 600 that includes an outer member 620. The outer member 620 is a coil similar to that of the outer member 520 of FIGS. 5A-5C. However, the elongated member 602 is configured differently than that of the elongated member 502 of FIGS. 5A-5C. The elongated member 602 of FIGS. 6A-6D extends to the distal end 624 of the outer member 620. The elongated member 602 includes a plurality of ports 604 at the distal portion 606. As previously discussed, the ports 604 can extend from the fluid passage 610 to an outer surface 614 of the elongated member 602 so that the fluid passage 610 can be in fluid communication with the secondary passage 522 of the outer member 620. The guide wire 600 can also include a sheath 630 over the proximal portion of the outer member 620, as discussed with regard to FIGS. 5A-5C. Furthermore, as shown in FIGS. 6A-6D, the proximal portion of the elongated member 602 can be in contact with the coil.

The elongated member 402, 502, 602 can comprise or be a first shape memory material, and the outer member 420, 520, 620 can comprise or be a second shape memory material. The second shape memory material may be different or the same as the first shape memory material. As such, the first and second shape memory materials may have two-way memory effect. Furthermore, the second shape memory material may have a transition temperature the same or substantially the same as the transition temperature of the first shape memory material. For example, the second shape memory material can have a transition temperature less than the body temperature. Alternatively, as discussed above, only one of the elongated member 402, 502, 602 or the outer member 420, 520, 620 comprises or is a shape memory material.

Furthermore, although the elongated member 102, 202, 402, 502, 602 and/or the outer member 420, 520, 620 comprises a shape memory material, the elongated member 102, 202, 402, 502, 602 and/or the outer member 420, 520, 620 may be a composite with non-shape memory materials while still maintaining the shape memory effect. For example, the elongated member 102, 202, 402, 502, 602 and/or the outer member 420, 520, 620 may include a coating of a different material. For instance, an outer surface of guide wire 100, 200, 300, 400, 500, 600 may have a polymer coating such as polytetrafluoroethylene to reduce friction of the guide wire 100, 200, 300, 400, 500, 600.

Although the distal portions 206, 406, 506, 606 in FIGS. 2A, 2B and 4A-6D are shown with either a straight shape or a curved shape, the distal portion 206, 406, 506, 606 can be configured to have other shapes. For example, the distal portion 206, 406, 506, 606 can have shapes such as angled, "J" shaped, or twisted. Furthermore, although the distal portion 206, 406, 506, 606 is described as having a first shape and a second shape, the distal portion 206, 406, 506, 606 can have other shapes as well. In particular, as the distal portion 206, 406, 506, 606 transitions between the first shape and the second shape, the distal portion 206, 406, 506, 606 can have other shapes. Furthermore, the amount of cooling can be controlled to control the amount shape change the distal portion 206, 406, 506, 606 undergoes. Thus, the degree of shape change can be controlled with control of the flow rate and/or the temperature of the fluid. The fluid supply 108 can be used to control flow rate and/or temperature of the fluid. For example, the fluid supply 108 can include a pump and/or a cooling system for the fluid.

An exemplary method of using a guide wire described herein can include inserting the guide wire into a body channel and navigating the guide wire through the body channel. After the distal portion of the guide wire has reached a location in which the distal portion of the guide wire is desired to be changed, fluid can be flowed through the elongated member in order to cool the distal portion of the guide wire so that the guide wire changes from a first shape (e.g., uncooled shape) to a second shape (e.g., cooled shape). The guide wire can then be navigated through the body channel. The cooling can be started or stopped any number of times to change the shape of the distal portion of the guide wire during the navigation of the guide wire through the body channel. Furthermore, the flow rate of the fluid can be slowed or sped up instead of completely stopped or started in order to provide other shapes.

In an alternative exemplary method, immediately or soon after the guide wire has been inserted into a body channel, fluid can be flowed through the elongated member in order to cool the distal portion so that the distal portion of the guide wire has a first shape (e.g., cooled shaped). After the distal portion has reached a location in which the distal portion of the guide wire is desired to be changed, fluid flow can be stopped or slowed so that the distal portion rises in temperature and transitions to a second shape (e.g., uncooled shape). The guide wire can then be navigated through the body channel. The flow rate of the fluid can be stopped, slowed, started, or sped up any number of times to change the shape of the distal portion of the guide wire during the navigation of the guide wire through the body channel. Thus, in view of the above example, the shape that the distal portion has primarily while navigating though the body channel can be either by cooling or non-cooling while shape that the distal portion has secondarily can be the opposite.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. While each embodiment described herein may refer only to certain features and may not specifically refer to every feature described with respect to other embodiments, it should be recognized that the features described herein are interchangeable unless described otherwise, even where no reference is made to a specific feature. Furthermore, the advantages described above are not necessarily the only advantages of the invention, and it is not necessarily expected that all of the described advantages will be achieved with every embodiment of the invention.

The invention claimed is:

1. A guide wire comprising:
   an elongated member defining a longitudinal axis and having a proximal portion, a distal portion, a diameter, and
   a fluid passage included within the elongated member and configured to transport a fluid from the proximal portion to the distal portion, and
   a fluid supply configured to supply fluid to the fluid passage in the elongated member, where the fluid supply includes at least one of a pump and a cooling system to control at least one of a flow rate and a temperature of the fluid,
   wherein the distal portion of the elongated member comprises a shape memory material with two way memory effect, the shape memory material having a transition temperature less than a body temperature such that the distal portion has a first shape at the body temperature and a second shape different from the first shape at a temperature less than the transition temperature, the distal portion pointing in a first direction when the distal portion has the first shape and pointing in a second direction different from the first direction when the distal portion has the second shape, and
   wherein the temperature of the shape memory material in the distal portion of the elongated member is configured to be changed by the effect of fluid transported in the fluid passage, to selectively cause the distal portion to take the first shape or the second shape without a change in the diameter of the elongated member, where at least one of the first shape and the second shape is curved relative to the longitudinal axis.

2. The guide wire of claim 1, wherein the shape memory material is nitinol, and the transition temperature is a temperature at which the nitinol completes a phase change from martensite to austenite.

3. The guide wire of claim 1, wherein the shape memory material is nitinol, and the transition temperature is a temperature at which the nitinol begins a phase change from austenite to martensite.

4. The guide wire of claim 1, wherein the shape memory material is nitinol, and the transition temperature is a temperature at which the nitinol begins a phase change from martensite to austenite.

5. The guide wire of claim 1, wherein the transition temperature is between 30° C. and 36° C.

6. The guide wire of claim 1, wherein the distal portion comprises a port extending from the fluid passage to an outer surface of the elongated member.

7. The guide wire of claim 6, wherein the port comprises a plurality of ports along a length of the distal portion.

8. The guide wire of claim 1, wherein the elongated member further comprises a return passage in fluid communication with the fluid passage to transport fluid from the distal portion to the proximal portion, wherein the return passage and the fluid passage are fluidly sealed from an outer surface of the guide wire.

9. The guide wire of claim 8, further comprising an outer member having a secondary passage being the return passage, the elongated member disposed within the secondary passage.

10. A guide wire comprising:
    an elongated member defining a longitudinal axis and having a proximal portion, a distal portion, a diameter, and
    a fluid passage included within the elongated member and configured to transport a fluid from the proximal portion to the distal portion, and
    a fluid supply configured to supply fluid to the fluid passage in the elongated member, where the fluid supply includes at least one of a pump and a cooling system to control at least one of a flow rate and a temperature of the fluid,
    wherein the distal portion of the elongated member comprises a shape memory material with two way memory effect, the shape memory material having a transition temperature less than a body temperature such that the distal portion has a first shape at the body temperature and a second shape different from the first shape at a temperature less than the transition temperature, the distal portion pointing in a first direction when the distal portion has the first shape and pointing in a second direction different from the first direction when the distal portion has the second shape,
    wherein the temperature of the shape memory material in the distal portion of the elongated member is configured to be changed by the effect of fluid transported in the fluid passage, to selectively cause the distal portion to take the first shape or the second shape without a change in the diameter of the elongated member, where in the first shape the distal portion points in a direction along the longitudinal axis and the second shape is curved relative to the longitudinal axis and the distal portion points in a direction away from the longitudinal axis, and wherein the guide wire further comprises an outer member having a secondary passage, the elongated member at least partially disposed within the secondary passage.

11. The guide wire of claim 10, wherein the shape memory material is a first shape memory material, and the outer member comprises a second shape memory material with two way memory effect, the second shape memory material having a transition temperature less than the body temperature.

12. The guide wire of claim 11, wherein the transition temperature of the second shape memory material is substantially the same as the transition temperature of the first shape memory material.

13. The guide wire of claim 10, wherein the outer member comprises an opening extending from the secondary passage to an outer surface of the outer member.

14. The guide wire of claim 13, wherein outer member comprises a coil having windings spaced a distance from one another.

15. The guide wire of claim 14, wherein the shape memory material is a first shape memory material, and the coil comprises a second shape memory material with two way memory effect, the second shape memory material having a transition temperature less than the body temperature.

16. The guide wire of claim 14, wherein the coil extends along the proximal portion and the distal portion of the elongated member, and the guide wire further comprises a tubular sheath covering a proximal portion of the coil while a distal portion of the coil is uncovered by the tubular sheath.

17. The guide wire of claim 14, wherein the distal portion of the elongated member comprises a port extending from the fluid passage to an outer surface of the elongated member.

18. The guide wire of claim 17, wherein the distal portion of the elongated member is radially spaced inward from the coil a distance.

19. The guide wire of claim 18, wherein the proximal portion of the elongated member is in contact with the coil.

20. The guide wire of claim 10, wherein a distal end of the elongated member is engaged with a distal end of the outer member.

* * * * *